(12) United States Patent
Landi

(10) Patent No.: US 10,937,538 B2
(45) Date of Patent: Mar. 2, 2021

(54) ASSESSMENT AND ADVICE ON NUTRITION AND ENDURANCE

(71) Applicant: NESTEC S.A., Vevey (CH)

(72) Inventor: Francesco Landi, Rome (IT)

(73) Assignee: Societe des Produits Nestle S.A., Vevey (CH)

(*) Notice: Subject to any disclaimer, the term of this patent is extended or adjusted under 35 U.S.C. 154(b) by 406 days.

(21) Appl. No.: 14/766,623

(22) PCT Filed: Feb. 3, 2014

(86) PCT No.: PCT/EP2014/052031
§ 371 (c)(1),
(2) Date: Aug. 7, 2015

(87) PCT Pub. No.: WO2014/122091
PCT Pub. Date: Aug. 14, 2014

(65) Prior Publication Data
US 2016/0004842 A1    Jan. 7, 2016

Related U.S. Application Data

(60) Provisional application No. 61/762,666, filed on Feb. 8, 2013.

(30) Foreign Application Priority Data

Feb. 8, 2013  (EP) .................................. 13154533

(51) Int. Cl.
*G06F 19/00* (2018.01)
*G06Q 50/22* (2018.01)
(Continued)

(52) U.S. Cl.
CPC ......... *G16H 20/30* (2018.01); *G06Q 10/0631* (2013.01); *G16H 20/60* (2018.01); *G16H 50/20* (2018.01); *G16H 50/30* (2018.01)

(58) Field of Classification Search
CPC ............. G06F 19/3475; G06F 19/3431; G06F 19/3481
See application file for complete search history.

(56) References Cited

U.S. PATENT DOCUMENTS

| 5,412,560 A * | 5/1995 | Dennison | G06F 19/3475 |
| | | | 128/921 |
| 2003/0226695 A1* | 12/2003 | Mault | A61B 5/0002 |
| | | | 177/25.16 |

(Continued)

FOREIGN PATENT DOCUMENTS

| CN | 1723838 A | 1/2006 |
| CN | 101059822 A | 10/2007 |

(Continued)

OTHER PUBLICATIONS

Purser, Jama L., Morris Weinberger, Harvey J. Cohen, Carl F. Pieper, Miriam C. Morey, Tracy Li, G. Rhys Williams, and Pablo Lapuerta; Walking speed predicts health status and hospital costs for frail elderly male veterans; Jul. 2005; VA Research Development; vol. 42 No. 4, p. 535-546; https://www.rehab.research.va.gov/jour/05/42/4/purser.html.*

(Continued)

*Primary Examiner* — Eddy Saint-Vil
*Assistant Examiner* — William D Ermlick
(74) *Attorney, Agent, or Firm* — K&L Gates LLP

(57) ABSTRACT

The present invention relates to a new integrated, holistic approach to empower older adults to enhance their quality of life and independence through a personalized lifestyle and nutrition program. This is achieved by measuring the physical status of the adults with respect to endurance/functionality. In addition, their nutritional status is assessed. Based on those assessments recommendations are provided with respect to particular exercise programs and nutrients that (Continued)

support the functions of the body. These methods can be implemented as a software program and executed on computer systems.

10 Claims, 1 Drawing Sheet

(51) Int. Cl.
*G06Q 10/06* (2012.01)
*G16H 50/20* (2018.01)
*G16H 50/30* (2018.01)
*G16H 20/30* (2018.01)
*G16H 20/60* (2018.01)

(56) References Cited

U.S. PATENT DOCUMENTS

| | | | | |
|---|---|---|---|---|
| 2005/0113649 | A1* | 5/2005 | Bergantino | G06F 19/3475 600/300 |
| 2006/0074279 | A1* | 4/2006 | Brover | G06F 19/3475 600/300 |
| 2006/0084847 | A1* | 4/2006 | Reed | A61B 5/0002 600/300 |
| 2006/0199155 | A1* | 9/2006 | Mosher | G09B 19/0092 434/127 |
| 2008/0086318 | A1* | 4/2008 | Gilley | G06Q 10/06 705/319 |
| 2010/0049095 | A1 | 2/2010 | Bunn et al. | |
| 2010/0204016 | A1* | 8/2010 | Chiu | G06F 19/3481 482/9 |
| 2010/0216098 | A1* | 8/2010 | Montgomery | G09B 19/0092 434/127 |
| 2013/0006063 | A1* | 1/2013 | Wang | G06F 19/3406 600/300 |
| 2013/0158368 | A1* | 6/2013 | Pacione | G06F 19/3418 600/301 |
| 2013/0216982 | A1* | 8/2013 | Bennett | G09B 5/00 434/127 |
| 2013/0261183 | A1* | 10/2013 | Bhagat | A23L 1/296 514/560 |
| 2014/0129243 | A1* | 5/2014 | Utter, II | G06F 19/345 705/2 |
| 2014/0243686 | A1* | 8/2014 | Kimmel | A61B 5/1114 600/476 |
| 2014/0344192 | A1* | 11/2014 | Akai | G06F 19/3475 706/11 |
| 2015/0012295 | A1* | 1/2015 | Mahoney | G06F 19/345 705/3 |
| 2015/0220697 | A1* | 8/2015 | Hunt | G06F 19/3475 705/2 |

FOREIGN PATENT DOCUMENTS

| | | |
|---|---|---|
| CN | 201572084 U | 9/2010 |
| CN | 102438519 A | 5/2012 |
| CN | 102902881 A | 1/2013 |
| JP | H11161725 A | 6/1999 |
| JP | 2006031433 | 2/2006 |
| JP | 2008026950 | 2/2008 |
| JP | 2008062071 | 3/2008 |
| JP | 2010198514 | 9/2010 |

OTHER PUBLICATIONS

MNA Mini Nutritional Assessment; Mar. 15, 2008; Nestle Nutrition Institute; https://wweb.archive.org/web/20080315114435/http://www.mna-elderly.com/default.html.*

Bowden, Mark G., Chitralakshmi K. Balasubramanian, Andrea L. Behrman, Steven A. Kautz; Validation of a Speed-Based Classification System Using Quantitative Measures of Walking Performance Poststroke; Oct. 29, 2008; The American Society of Neurorehabilitation; vol. 22, issue 6, p. 672-675; http://journals.sagepub.com/doi/pdf/10.1177/1545968308318837.*

Office Action for corresponding Japanese application No. 2015-556458; dated Jan. 30, 2018; (10 pages).

* cited by examiner

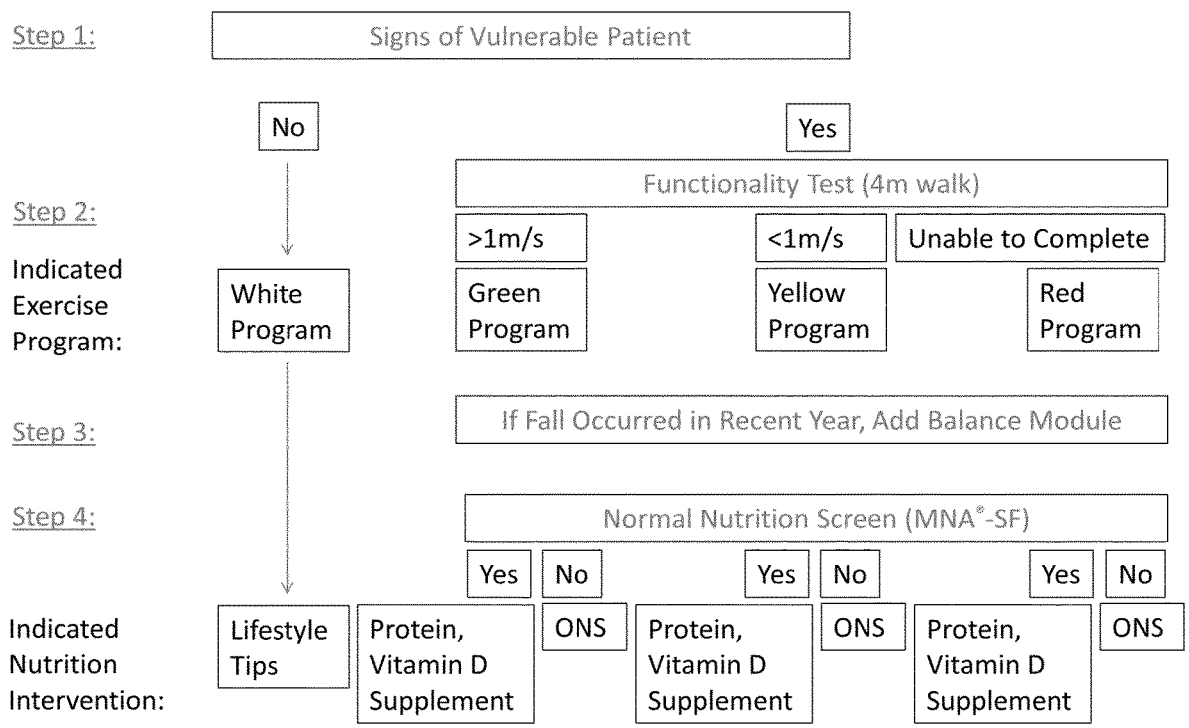

ASSESSMENT AND ADVICE ON NUTRITION AND ENDURANCE

CROSS REFERENCE TO RELATED APPLICATIONS

The present application is a National Stage of International Application No. PCT/EP2014/052031, filed on Feb. 3, 2014, which claims priority to European Patent Application No. 13154533.7, filed on Feb. 8, 2013, and U.S. Provisional Application Ser. No. 61/762,666, filed on Feb. 8, 2013, the entire contents of which are being incorporated herein by reference.

BACKGROUND

For the past decades the Western world and Japan observe a rise of the number of the elderly in the population. It is often observed that those elderly become frail and dependent on assistance. However, the development of frailty does not need to be inevitable. Appropriate advice and training of older adults can prevent many negative developments. It is therefore desirable to assist the elderly in maintaining or achieving an acceptable health status for a better quality of life. Previous approaches to the problem have generally involved providing unpersonalized, general recommendations to specific populations without fair consideration for potentially important differences between individuals in regards to their nutritional intake and physical capabilities. It is more likely that a personalized approach with exercise and specific nutrient would be more efficient in enhancing musculoskeletal health. Such personalized recommendations are possible at the only condition of having done a personalized evaluation of both the nutritional state and the physical ability/condition of the subject. Therefore, a novel approach is required for being able to perform such an evaluation in a short period of time. This approach should provide a coordinated method for providing advice and training to older adults.

SUMMARY

The invention relates to a computer-implemented method for determining the physical status of a subject comprising: providing a classification system for the parameters nutrition and physical endurance of said subject; assessing and scoring values of said parameters in said subject; using the obtained scores to classify the subject into classes with respect to each of said parameters; and using said determined classes for each parameter to determine the physical status of said subject.

In the first step of said method it can be determined whether the subject is suitable for being subjected to the method of the invention. The subject can be an older subject, preferentially a human subject being older than 65 years. The physical status can be assessed by having a subject walk for a predetermined time or over a certain distance. The parameter nutrition can be assessed by the MNA and/or the evaluation of daily protein intake. The steps of the method can be performed within 20 or 90 minutes, preferably less than 30 minutes. The steps can be repeated in defined intervals, preferentially every 8-16 weeks.

In a further embodiment the invention relates to a computer-implemented method for improving the physical status of a subject comprising: determining the physical status of a subject according to any of the above described methods; providing recommendations for the subject with respect to nutrition and physical endurance and/or resistance based on the determined scores wherein the nutrition contains bioactive nutrients improving physical endurance.

Based on the determined class for the parameter physical status a particular exercise program can be recommended, wherein the exercise program is different for each determined class.

In a further embodiment a system for determining the physical status of a subject, said system comprising a computer: said computer stores a data based comprising a classification system for the parameters nutrition and physical endurance of a subject; said computer stores a software program having instructions causing the computer to receive and store the values of said parameters in said subject; to score values of said parameters in said subject, to use the obtained scores to classify the subject into classes with respect to each of said parameters, and to output said class and thereby indicating the physical status of said subject based on said classes.

In a further embodiment the invention relates to a system for facilitating the improvement of a physical status of a subject, said system comprising a computer: said computer stores a data based comprising a classification system for the parameters nutrition and physical status of a subject; said computer stores a software program having instructions causing the computer to receive and store the values of said parameters in said subject, to score values of said parameters in said subject, to use the obtained scores to classify the subject into classes with respect to each of said parameters, relating recommendations for the subject with respect to nutrition and physical endurance and/or resistance based on the determined classes, and outputting said recommendations.

In a further embodiment the invention relates to a method for personalizing elderly care comprising the steps of: creating a database relating to physical functional tests and their validity to identifying the overall physical status of select elderly patient populations; storing the database on a computer; executing a computer program causing the computer to determine viable functional test results relating to physical status and to the nutritional status in specific elderly patient populations, the test results including end points relating to nutrition and physical state; and executing a program that uses the end points to generate guidelines based on nutrition and exercise test results that can be used to personalize a nutrition and exercise program for a member of the specific elderly population.

At least two or three different programs can be used by the computer. The computer program can be executed by the computer to personalize the nutrition and exercise program for the member. The computer program can also contain a step relating the physical status to recommendations for the member and outputting those recommendations. During the program the member can be monitored to determine nutrition and physical status. Depending on the results of the monitoring the nutrition and exercise program can be modified. The exercise programs can be endurance or resistance exercise programs adapted to the particular needs of the member.

BRIEF DESCRIPTION OF THE FIGURE

The FIGURE schematically shows has the physical status of person is assessed with respect to physical state and the nutrition. Based on the categorization following from those tests individual recommendations for further training and nutritional intervention can be made.

DEFINITIONS

Older people/adults or elderly are defined to be human beings that are older than 60. In particular, they can have an age above 65, 70, 75, 80, 85, or 90. They can also have an age between 60 and 90 years, 65 and 90, 70 and 90 years, 75 and 90 years, 80 and 90 years, 85 and 90 years, or between 60 and 85 years, 60 and 80 years, 60 and 75 years, 60 and 70 years, 60 and 65 years. Any combination of the upper and lower limits regarding age as defined above is also considered to be disclosed here.

About is defined to define a range in relation to a particular numerical value. The range can be +/−10%, +/−7.5%, +/−5%, +/−2.5%, or +/−1% in relation to the particular numerical value.

Scoring is a method by which a numerical value obtained by a test method performed by a subject is related/transformed to a further piece of information usually a further number to give standardized information on the performance of said subject in said test. For example, the walking speed of a subject might be 2 m/sec. For a speed of 0-1 m/sec the score has been defined to be 1. For a speed of above 1 m/sec to 2.5 m/s the score has been determined to be 2 and for above 2.5 m/sec the score has been defined to be 3. Thus, the walking speed of the subject can be scored to be 2.

A Physical Activity Readiness Questionnaire (PAR-Q) is an established and publicly available 1-page form to see if you should check with your physician before becoming much more physically active.

DETAILED DESCRIPTION OF THE INVENTION

The section headings serve to clarify the subject matter and should not be interpreted to limit the subject matter. If ranges of values are disclosed each individual value is considered to be covered by the range, in particular, each integer number.

Basic Concept of Invention

The present invention relates a new integrated, holistic approach to empower older adults to enhance their quality of life and independence through a personalized lifestyle and nutrition program. The invention relates to tools for achieving these goals. In particular, the aim of the invention is to propose a test system for evaluating the physical condition (and the nutritional state) of older subjects to be able to propose personalized recommendations for a personalized training program and nutritional recommendations.

In a first aspect, a method is provided that allows to assess the health status of a person, in particular an older adult, by a variety of tests for evaluating individual aspects of the health status. In a second aspect, the results of those evaluations are used to provide to those persons tested personalized advice on improving their health status.

The evaluation of the first aspect takes place by assessing two parameters. These parameters are nutrition and physical functionality. The values of these parameters are determined for each person individually. The determined values allow to score the persons into certain classes. For each group a predetermined advice for a nutritional and training program can be provided in the second aspect. It is important that based on the recommendations regarding a training program that aims to improve the strength or endurance of a person the nutritional needs need to be adapted. Furthermore, the choice of the nutritional program opens new potentials for adapted training programs. Thus, there is an interplay with respect to the factors strength or endurance of a person and the nutritional needs. This is the first time that the interrelation between these three factors is considered when addressing the needs of the elderly with respect to their health status. Moreover, the recommendations are provided on a personalized level tailored to the needs of the individual person.

Overview Over the Methods of the Invention

As mentioned above the beginning of the method resides in the assessment of the relevant parameters (physical state, nutrition).

Prior to this assessment the person might be individually tested for their readiness for the assessment method of the invention (Pre-assessment, program readiness e.g. with the PAR-Q questionnaire or determination with a frailty index). Depending on the result of the PAR-Q or frailty index, subjects will therefore do a walk test (e.g. the 4 m walk test) evaluating their gait speed related to their ability to follow the exercise program.

Preferentially, in a first step it is determined whether a patient shows signs of vulnerability. This can be done by determining whether a subject shows signs of frailty according to a frailty index. If the subject does not show signs of a vulnerable patient he can receive lifestyle suggestions in line with universal guidelines.

If the person does show signs of a vulnerable patient he can be subjected to further tests which are an endurance (functionality) test and a nutrition test screen. Based on these tests particular exercise programs and nutritionals recommendations are suggested or recommended.

Thus, the invention aims to assist people who are at risk of sliding into functional decline.

Thus, after the test for signs of a vulnerable patient, the physical capacity assessment is the measurement of the gait speed. Based on the achieved gait speed the subjects can be recommended different exercise programs. Optionally, if the subject has fallen in the year before the functionality test a balance module can be added.

In addition to the physical assessment a nutrition screen (e.g. MNA test) can be performed for each group identified in the functionality test. Based on said nutrition screen nutritional recommendations can be provided. In particular, oral nutritional supplements can be provided. These oral nutritional supplements can comprise protein or/and vitamin D.

In a preferred embodiment a subject can be assigned to one of four different exercise programs and provided with individual recommendations on nutritional intervention. These exercise programs and forms of nutritional intervention are described below.

Each person can enroll in a personalized nutrition and exercise program. This program will last for 8 to 26, 12-20, or about 16 weeks. After this personalized nutrition and exercise program is completed and a further main assessment comprising a endurance assessment and nutrition assessment can be performed. In this way progress of the person with regard to the measured parameters can be determined. Based on the report of the progress the personalized nutrition and exercise program can be modified or cancelled. Thus, the method of the invention allows to periodically modify the personalized nutrition and exercise program based on the results of the main assessment to optimize the benefit for the person. Accordingly, in an embodiment the invention relates to an reiterative process wherein based on the results of the main assessment an personalized nutrition and exercise program is chosen and the effects of said program are reassessed after a defined period and based on these reassessment the personalized nutrition and exercise program is modified. The last two steps can be performed at least 2, 3, 4, 5, 6, 7, 8, 9, 10 or more times. Prior to this feedback loop the method can comprise a pre-assessment to decide whether a person is eligible for the main assessment.

First Assessment

The first assessment test is a method that serves to evaluate whether a person is suitable to the subjected to the main assessment method. The first evaluation tests will generally impart less demanding test conditions on the persons to be tested. The test serves to identify signs of a vulnerable patient (see FIGURE step 1). The test can be, for example, a Physical Activity Readiness Questionnaire or preferentially a method to determine the frailty of a person.

The Physical Activity Readiness Questionnaire (PAR-Q) is a test which serves to quickly check that the tests and exercises that are proposed are medically safe from a cardiac point of view. The PAR-Q test can serve to identify signs of a vulnerable patient (see FIGURE, step 1). Depending on the PAR-Q result, subject can do a walk test (e.g. a 4 m walk test) to do a first evaluation of their physical capacity: they will have to do a walk over a certain distance where the person is asked to walk over said distance with his usual (comfortable) pace. The measured speed of the person over said distance allows to determine whether the person qualifies for the main assessment method. A measured value that is below a predetermined lower limit indicates that the person is not suitable for the main assessment. In those cases, the person is usually to frail and the person should undergo further medical examination, for example, performed by a geriatrician. A measured value that is above a predetermined upper limit indicates that the person is not suitable for the main assessment either. In those cases, the person is usually sufficiently healthy and thus does not need further recommendations regarding its lifestyle. A measured value that is between a predetermined lower limit and a predetermined upper limit indicates that the person is suitable for the main assessment.

In particular, embodiments the walk might be a walk having a length of between 2-6 m, 3-5 m, or 4 m. Preferentially, the walk has a length of 4 m. The lower limit as described above might be a value between 0.4 and 0.8 m/s, 0.5 and 0.7 m/s, or 0.6 m/s. The upper limit as described above might be a value between 1.3 and 1.7 m/s, 1.4 and 1.6 m/s m, or 1.5 m/s. In a preferred embodiment, the lower limit is 0.6 m/s and the upper limit is 1.5 m/s.

Alternatively and more preferred, the first assessment is directed to identifying signs of a vulnerable patient. This can be done buy use simply frailty tests that are known in the art. In particular, those frailty tests are considered here that are described by Morley et al. (J Nutr Health Aging. 2012 July; 16(7):601-8, "A simple frailty questionnaire (FRAIL) predicts outcomes in middle aged African Americans"), Subra et al. (The journal of nutrition, health & aging, October 2012, Volume 16, Issue 8, pp 714-720 "The integration of frailty into clinical practice: Preliminary results from the Gérontopôle", or Kalyani et al. (The journal of nutrition, health & aging, October 2012, Volume 16, Issue 8, pp 679-686 "Frailty status and altered dynamics of circulating energy metabolism hormones after oral glucose in older women"). As a result of this first assessment the subject can be either characterized of exhibiting sings of frailty or not exhibiting those signs. If the subject shows signs of frailty he can be subjected to the main assessment which allows to group or score the subjects into further sub-classes. If the subject does not show signs of frailty the subject can be directly provided with recommendations on exercise programs ("green program"). Optionally, the nutritional status of said subjects can be also determined.

Additional Assessment

Additional assessment method comprises an endurance assessment method and a nutrition assessment method. The assessment can also consider factors like age, sex, or the results of anamnesis of the person that is subjected to the tests. These factors can affect the scoring of the determined test values.

Endurance Assessment

The endurance (functionality) assessment method can comprise at least one test for assessing the endurance/functional abilities of a subject (e.g. ability to perform given activity of daily living task such as walking).

The functionality test can comprise at least one method for determining the endurance by having a person walk for a predetermined time or over a certain distance. In a preferred endurance assessment method the method comprises a walk test method.

In a preferred method, the person has to walk for 4 m. Subsequently, the gait speed is determined and dependent on the achieved gait speed the subject is assigned to a particular class. The subjects can be grouped into 2, 3, 4, or 5 classes. Thus, the classes can be defined by particular upper and lower limits for the achieved gait speed. Based on the determined class recommendations with respect to exercise programs can be made. Particular preferred are three classes. In case of three classes the boundaries/limits or the classes can be a gait speed of >1 m/s, <1 m/s and a class where the subjects are unable to complete the test. Based on these three classes into which the subjects are grouped exercise programs can be recommended. In the case of three groups three different exercise recommendations can be provided (e.g. named green, yellow and red program for the group that had a gait speed of >1 m/s, <1 m/s and a class where the subjects are unable to complete the program respectively).

Nutrition Assessment

The nutritional status of each subject which undergo the functionality test can be assessed by nutritional assessment. Particular useful are questionnaires like the Mini-Nutritional Assessment (MNA) or the short form of the Mini-Nutritional Assessment (MNA-SF).

The Mini-Nutritional Assessment (MNA®) is a validated nutrition screening and assessment tool that can identify geriatric patients age 65 and above who are malnourished or at risk of malnutrition. The MNA® was developed nearly 20 years ago and is the most well validated nutrition screening tool for the elderly. Originally comprised of 18 questions, the current MNA® now consists of 6 questions and streamlines the screening process. The current MNA® (see e.g. Skates J J, Anthony P S. Identifying geriatric malnutrition in nursing practice: the Mini Nutritional Assessment (MNA (R))—an evidence-based screening tool J Gerontol Nurs 2012; 38(3): 18-27; quiz 28-29 retains the validity and accuracy of the original MNA® in identifying older adults who are malnourished or at risk of malnutrition. The revised MNA® Short Form makes the link to intervention easier and quicker and is now the preferred form of the MNA® for clinical use.

Particularly preferred is the application of the MNA-SF to the subjects.

The MNA-SF takes into account five factors which are decline of food intake over the past 3 months, weight loss during the past 3 months, mobility, suffering from psychological stress or acute disease in the past 3 months, neuropsychological problems and a factor that is the body mass index (BMI) or if not available the calf circumference. Based on the scored results of the MNA-SF a subject can be grouped into the class "normal nutritional status" or "at risk of malnutrition"/"malnourished."

Additional Assessments

The main assessment can also comprise the consideration of other parameters like strength, age, sex, weight, height, or the anamnesis of the person that is subjected to the tests.

Recommendations on Exercise Programs

Based on the scores determined in the previous steps an exercise program is selected or recommended for the person. Lower scores are associated with less demanding exercise programs and higher scores result in the selection or recommendation of more demanding exercise programs. If the subject does not shows signs of a vulnerable patient, manages the 4 m walk at a higher speed than 1 m/s, and exhibits a normal nutritional status the subject can receive lifestyle suggestions in line with universal guidelines (designated: white exercise program).

If the subject does show signs of a vulnerable patient but manages the 4 m walk at a higher speed than 1 m/s the following (designated: green) exercise program can be indicated. This program can comprise aerobic a (endurance) exercise(s) (such as: walking, dance, swimming, gym equipment) at 3-6 days (d) per week (wk). The program can also comprise a strength exercise (e.g. lowerbody body weight exercises, hand weights 5 lb (3 kg), ankle weights) at 10 exercises per week (wk). The aerobic training can be progressed to 150 min/wk and strength exercise 2-3 d/wk. The intensity can also be progressed (perceived relative intensity). The exercise can be monitored via a log booklet. In general the green program will be performed at a moderate to vigorous intensity.

If the subject does show signs of a vulnerable patient and accomplishes the 4 m walk at less than 1 m/s the following exercise program can be indicated (designated: yellow exercise program): The program comprises an aerobic (endurance) exercise (such as: walking, dance). The program can also comprise a strength exercise (lowerbody body weight exercises) at 5 exercises per week. The aerobic training can be progressed to 75 min/wk and strength exercise 3 d/wk. The goal is to advance to the green program.

The exercise can be monitored via a log booklet. In general the yellow program will be performed at a moderate intensity.

If the subject does show signs of a vulnerable patient and is unable to do the 4 m walk, is not able to walk, wheelchair or bedridden the following program is indicated (designated: red exercise program): This program comprises an aerobic (endurance) exercise (such as: slow walking, slow dance if applicable). It can also comprise a strength exercise (lowerbody body weight exercises) at 2 exercises per week The goal is to advance to the yellow program.

The exercise can be monitored via a log booklet. In general the red program will be performed at a low intensity.

More demanding exercises are exercises which take longer or/and done with a higher intensity level or/and are repeated more often in a predetermined fixed time period than less demanding exercises. It is also an option to perform a "challenge" which is an exercise performed within a shorter period of time but with higher intensity compared to the exercises of the usual exercise programs.

If more than one test is used to classify the person into the system the scores might differ. These might be indicative of a physical imbalance between different tested areas of the body. In those cases the exercise unity might be adapted to train the area of the body that appears to be in a weaker physical condition.

Recommendations on Nutrition

Based on the classes obtained for the nutritional status certain nutritional recommendations can be provided to the persons. The nutritional recommendations aim at the maintenance or improvement of the physical parameters of the person that are important for the physical mobility of a person. In particular, these physical parameters are bone mass, muscle mass, muscle strength, integrity of joints. Thus, the nutrition should contain bioactive nutrients both in the form of a complete nutrition or in the form of supplemental nutritional agents. The bioactive nutrients of the invention have an effect on the maintenance of bone mass, muscle mass, muscle strength, integrity of joints, i.e. protect joints and/or improve the comfort of the person. Examples for bioactive nutrients are an increased protein supplementation, particular protein supplements (like whey protein), calcium, vitamin D etc. If the case a subject can be scored to the group of "normal nutritional status" a regular diet can be recommended while if the subject can be scored in the groups "at risk of malnutrition"/"malnourished" a diet can be recommended that is adapted to the needs of said subjects. In particular, a complete oral nutritional supplement (ONS) can be recommended. In a preferred embodiment, this ONS will comprise (supplemental) protein and/or vitamin D.

Computer Implemented Methods and System

Any of the above methods insofar as they relate to receiving, processing and outputting of data can be implemented as software programs and executed on computers.

The invention is directed to a computer implemented method for determining the physical status of a subject comprising: providing a database comprising a classification system for the parameters nutrition and physical endurance of said subject wherein the classification system associates numerically determined values of said parameter with scores for said values, and said system also associates said scores with classes and said system associates said classes with an indication of particular physical status, inputting values for said parameters which have been determined by functional physical tests in said subject, using said values to score those values for each parameter according to the database, using the obtained scores to classify the subject into classes with respect to each of said parameters according to said database, using said determined classes for each parameter to determine an indication of a physical status of said subject, and outputting said indication of the physical status for said subject.

The subject can be an older subject, preferentially a human subject being older than 65 years. The parameter endurance can be assessed by at least one endurance test. The endurance test can be selected from the group consisting of measuring the distance achieved in a walk test.

The parameter nutrition can be assessed by at least one nutrition test. The nutrition test can be the MNA.

The computer implemented method can comprise additional steps. The database might then also comprise recommendations for the subject with respect to nutrition, physical endurance, and optionally physical strength based on the determined classes. The method might then also contain the step of associating the determined classes with the specific recommendations and outputting those recommendations.

The exercise program can be different for each determined class but also according to individual preferences.

In a further embodiment a system for determining the physical status of a subject is disclosed, said system comprising a computer: said computer stores a data base comprising a classification system for the parameters nutrition and physical status of a subject; said computer stores a software program having instructions causing the computer to receive and store the values of said parameters in said subject; to score values of said parameters for said subject; to use the obtained scores to classify the subject into classes with respect to each of said parameters; calculate a value for the physical status of said subject based on said classes.

Furthermore, a system for facilitating the improvement of a physical status of a subject is disclosed, said system comprising a computer said computer stores a data based comprising a classification system for the parameters nutrition and physical status of a subject; said computer stores a data base comprising a classification system for the parameters nutrition and physical status of a subject; said computer stores a software program having instructions causing the computer to receive and store the values of said parameters in said subject; to score values of said parameters for said subject; to use the obtained scores to classify the subject into classes with respect to each of said parameters; calculate a value for the physical status of said subject based on said classes, associating said value of the physical status with particular recommendation for said subject, outputting recommendations for the subject with respect to nutrition, physical endurance, and optionally physical strength based on the determined classes.

In a further embodiment a method for personalizing elderly care comprising the steps of: creating a database relating to physical functional tests and their validity to identifying the overall physical status of select elderly patient populations; storing the database on a computer; executing a computer program causing the computer to determine viable functional test results relating to endurance in specific elderly patient populations, the test results including end points relating to nutrition and physical conditions; and executing a program that uses the end points to generate guidelines based on nutrition and physical test results that can be used to personalize a nutrition and exercise program for a member of the specific elderly population.

At least two or three different programs are used by the computer.

The computer program can be executed by the computer to personalize the nutrition and exercise program for the member. The computer program can also contain a step relating the physical status to recommendations for the member and outputting those recommendations. During the program the member can be monitored to determine nutrition and physical staus. Depending on the results of the monitoring the nutrition and exercise program can be modified. The exercise programs can be endurance and strength exercise programs adapted to the particular needs of the member.

Example

Example: Algorithm

An overview over the algorithm to be used in the practice of the invention is provided in the FIGURE to which this example refers.

The patient can be first tested whether he shows any signs of vulnerability or to which degree.

If the patient does not show any signs of vulnerability the white program is the indicated exercise program (currently active & healthy). Currently active receive lifestyle suggestions in line with universal guidelines.

If the patient shows signs of vulnerability the patient can be subjected to an endurance test (eg. functionality test, like a 4 m walk).

If the patient manages the 4 m walk at a higher speed than 1 m/s the green exercise program can be indicated:

This green program comprises

Aerobic (endurance) exercise (such as: walking, dance, swimming, gym equipment) at 3-6 d/wk Strength exercise (lowerbody body weight exercises, hand weights 5 lb (3 kg), ankle weights) at 10 exercises per week (wk)

The aerobic training can be progressed to 150 min/wk and strength exercise 2-3 d/wk.

The intensity can also be progressed (perceived relative intensity). The exercise can be monitored via a log booklet. In general the green program will be performed at a moderate to vigorous intensity.

The yellow program is indicated if the 4 m walk is accomplished at less than 1 m/s:

This yellow program comprises

Aerobic (endurance) exercise (such as: walking, dance)

Strength exercise (lowerbody body weight exercises) at 5 exercises per week

The aerobic training can be progressed to 75 min/wk and strength exercise 3 d/wk.

The goal is to advance to the green program.

The exercise can be monitored via a log booklet. In general the yellow program will be performed at a moderate intensity.

The red program is indicated if the subject is unable to do the 4 m walk, not able to walk, wheelchair or bedridden:

This red program comprises

Aerobic (endurance) exercise (such as: slow walking, slow dance if applicable)

Strength exercise (lowerbody body weight exercises) at 2 exercises per week

The goal is to advance to the yellow program.

The exercise can be monitored via a log booklet. In general the red program will be performed at a low intensity.

The nutrition intervention will depend on the determined value for the parameter nutrition.

The evaluation of the nutritional status (well nourished, at risk of malnutrition, malnourished) can be assessed using the MNA.

If the value is considered to be normal a regular diet can be recommend. For patients at risk or are malnourished a complete oral nutritional supplement (ONS) can be recommended which comprises for example supplemental protein or vitamin D.

The invention claimed is:

1. A method for treating frailty of a subject, the method comprising:
   (a) measuring a speed of walk of the subject over a predetermined distance and determining that the speed of walk is between a predetermined upper limit and a predetermined lower limit, wherein the predetermined upper limit is between 1.3 and 1.7 m/s, and the predetermined lower limit is between 0.4 and 0.8 m/s;
   (b) performing a computer-implemented process comprising:
      providing a database comprising a classification system for parameters of nutrition and physical endurance of the subject, wherein the classification system associates numerically determined values of the parameters with scores for the values, and the classification system associates the scores with classes and also associates the classes with indications of a physical status based on physical parameters selected from the group consisting of bone mass, muscle mass, muscle strength, integrity of joints, and combinations thereof;

inputting values of the parameters of the subject, the values of the parameters of physical endurance are determined by functional physical tests on the subject;

scoring the values according to the database to obtain scores for the nutrition and the physical endurance of the subject;

using the scores to classify the subject into classes with respect to each of the parameters according to the database; and providing recommendations for the subject based on the classes, the recommendations are for the nutrition and the physical endurance of the subject; and the method further comprising administering bioactive nutrients to the subject according to the recommendations to improve the physical parameters of the subject, and at least one of the bioactive nutrients administered to the subject according to the recommendations is selected from the group consisting of protein, calcium, and vitamin D.

2. The method of claim 1 wherein the subject is a human older than 65 years.

3. The method according to claim 1 wherein the computer-implemented process comprises assessing the physical endurance of the subject by measuring a speed of a walk of the subject over a predetermined time period or over a predetermined distance.

4. The method according to claim 1 wherein the nutrition of the subject is assessed by Mini-Nutritional Assessment and/or evaluation of daily protein intake.

5. The method according to claim 1 wherein the steps of the computer-implemented process are performed within 20 minutes.

6. The method according to claim 1 wherein steps of the computer-implemented process are repeated in defined intervals.

7. The method according to claim 1 wherein the recommendations identify a particular exercise program based on the class for the physical endurance of the subject, wherein the exercise program is different for each determined class.

8. The method according to claim 1 wherein the classes comprise at least one class indicative of a subject who is malnourished or at risk of malnutrition and for which the recommendations identify an oral nutritional supplement comprising at least one of protein or vitamin D.

9. The method according to claim 1, wherein the predetermined upper limit is between 1.4 and 1.6 m/s.

10. The method according to claim 1, wherein the predetermined upper limit is 1.5 m/s.

* * * * *